(12) United States Patent
Eymery et al.

(10) Patent No.: US 12,239,815 B2
(45) Date of Patent: Mar. 4, 2025

(54) TUB FOR THE PACKAGING OF A PLURALITY OF NESTS OF PLUNGER STOPPERS WITH GUIDING FEATURES ENSURING A RELIABLE LOCATION OF THE NESTS WITHIN THE TUB

(71) Applicant: Becton Dickinson France, Le Pont-de-Claix (FR)

(72) Inventors: Anaïs Eymery, Saint-Georges-de-Commiers (FR); Clémentine Le Loc'h, Meylan (FR); Ferdinand Lavigne, Seyssinet-Pariset (FR); Gildas Esnault, Grenoble (FR); Laurent Jacquier, Saint Cassien (FR); Thomas Magguili, Vizille (FR)

(73) Assignee: Becton Dickinson France, Le Pont-de-Claix (FR)

( * ) Notice: Subject to any disclaimer, the term of this patent is extended or adjusted under 35 U.S.C. 154(b) by 5 days.

(21) Appl. No.: 18/273,616

(22) PCT Filed: Jan. 26, 2022

(86) PCT No.: PCT/EP2022/051755
§ 371 (c)(1),
(2) Date: Jul. 21, 2023

(87) PCT Pub. No.: WO2022/162003
PCT Pub. Date: Aug. 4, 2022

(65) Prior Publication Data
US 2024/0091433 A1   Mar. 21, 2024

(30) Foreign Application Priority Data
Jan. 26, 2021  (EP) .................................... 21305102

(51) Int. Cl.
*A61M 5/00* (2006.01)
*B65D 25/10* (2006.01)

(52) U.S. Cl.
CPC ........... *A61M 5/008* (2013.01); *B65D 25/108* (2013.01)

(58) Field of Classification Search
CPC ......... A61M 5/00; A61M 5/008; B65D 25/10; B65D 25/108
USPC ...................................................... 206/366
See application file for complete search history.

(56) References Cited

U.S. PATENT DOCUMENTS

| | | | |
|---|---|---|---|
| 6,250,052 B1 | 6/2001 | Porfano et al. | |
| 6,534,015 B1 | 3/2003 | Viot et al. | |
| 8,453,838 B2 | 6/2013 | Hill | |
| 9,095,848 B2 | 8/2015 | Carrel et al. | |

(Continued)

FOREIGN PATENT DOCUMENTS

| | | |
|---|---|---|
| EP | 2476448 A1 | 7/2012 |
| EP | 3524293 A1 | 8/2019 |
| WO | 2012143533 A1 | 10/2012 |

*Primary Examiner* — Bryon P Gehman
(74) *Attorney, Agent, or Firm* — The Webb Law Firm

(57) ABSTRACT

A nest and tub arrangement for the storage of medical device components including a tub having a plurality of guide elements extending from at least one surface of the tub and into the interior of the tub, and at least one nest having a plurality of receptacles for the storage of a plurality of medical device components therein. The at least one nest is sized and configured for placement within the tub such that the plurality of guide elements align and removably retain the at least one nest within the tub.

12 Claims, 12 Drawing Sheets

(56) References Cited

U.S. PATENT DOCUMENTS

| | | | | |
|---|---|---|---|---|
| 9,963,259 B2* | 5/2018 | Deutschle | ............ | B65D 25/108 |
| 10,023,358 B2 | 7/2018 | Carrel | | |
| 10,800,557 B2* | 10/2020 | Narvekar | .............. | A61M 5/008 |
| 10,918,784 B2 | 2/2021 | Yoshida | | |
| 11,472,602 B2* | 10/2022 | Komann | ................ | A61M 5/008 |
| 12,098,018 B2* | 9/2024 | Nau | ..................... | B65D 25/108 |
| 2017/0008001 A1 | 1/2017 | Motadel et al. | | |

* cited by examiner

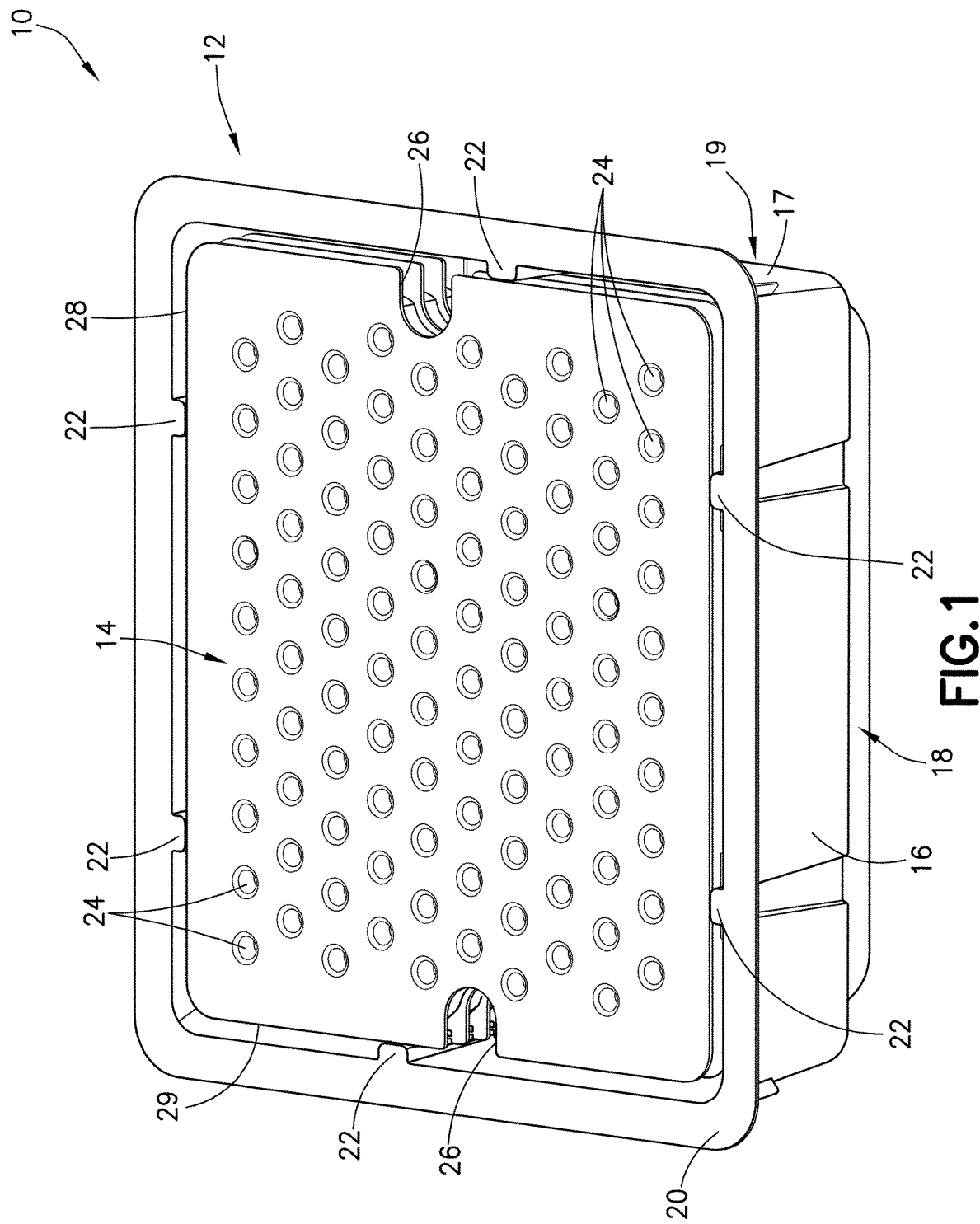

TUB FOR THE PACKAGING OF A PLURALITY OF NESTS OF PLUNGER STOPPERS WITH GUIDING FEATURES ENSURING A RELIABLE LOCATION OF THE NESTS WITHIN THE TUB

CROSS-REFERENCE TO RELATED APPLICATIONS

This application is the United States national phase of International Application No. PCT/EP2022/051755 filed Jan. 26, 2022, and claims priority to European priority application no. EP 21305102.2, entitled "A Tub for the Packaging of a Plurality of Nests of Plunger Stoppers with Guiding Features Ensuring a Reliable Location of the Nests Within the Tub", filed Jan. 26, 2021, the entire disclosures of which are hereby incorporated by reference in their entirety.

BACKGROUND

Field of the Disclosure

The present disclosure relates generally to nest and tub arrangements for the packaging of plunger stoppers used in medical devices such as, e.g., syringes. More particularly, the present disclosure relates to a tub for the packaging of at least one nest configured to hold a plurality of plunger stoppers, wherein the tub includes guiding features ensuring a reliable location of the at least one nest therein.

Description of the Related Art

As is known in the art, transfer or storage devices for delivery or storage of a medicament, drug, or vaccine (such as, e.g., syringes) utilize a plunger stopper in contact with an inside surface of a generally tubular syringe barrel in order to draw a substance into (or expel a substance from) the device by way of a plunger rod.

Currently, many such devices are filled and assembled using automated filling machines. Not only do such machines improve productivity and accuracy, but they also provide for a substantially sterile and aseptic filling environment. The various components of the devices (e.g., plunger stoppers, syringe barrels, etc.) are separately provided within the filling machines to enable at least some level of automated assembly.

Typically, a plurality of plunger stoppers are provided in bags or in nests (which are also provided in bags) to be accessed by the filling machine during assembly. Conversely, the syringe barrels are generally packaged in nests having numerous "chimneys" formed therein to hold the barrels, with each nest configured to be held at least partially within a tub when introduced into the filling machine.

While the current nests for syringe barrels are specifically designed for use with tubs, the current nests designed for holding plunger stoppers are not configured for use with a specific tub profile, nor do they fit securely within the tubs used for syringe barrels. In some automated filling machines, the lack of a tub for holding the nests of plunger stoppers does not present an issue. However, in other, more recently-designed filling equipment (such as, e.g., the Vanrx SA25 robotic aseptic filling workcell from Vanrx Pharmasystems Inc.), only components packaged in both nests and tubs are capable of being handled.

Furthermore, as noted above, currently-available nests for plunger stoppers are not designed to be held within existing tub designs. Thus, if one were to attempt to utilize existing nests and tubs together in relation to plunger stoppers, the combination may result in unreliable positioning and unwanted movement of the nests within the tub, which would be problematic for the robotic handling of the nests within the filling equipment. Documents WO2021/143533A1, EP2476448A1 and EP3524293A1 relate to packaging for medical containers.

SUMMARY

In view of the foregoing, there exists a need for nests designed specifically for plunger stoppers, as well as a tub designed specifically to accommodate a plurality of such nests. Additionally, there exists a need for a tub and/or nest configured to ensure reliable alignment of a plurality of nests within each tub.

Embodiments of the present disclosure are directed to a nest and tub arrangement for the storage of medical device components. The nest and tub arrangement may include a tub comprising a plurality of guide elements extending from at least one surface of the tub and into the interior of the tub, and at least one nest having a plurality of receptacles for the storage of a plurality of medical device components therein. The at least one nest may be sized and configured for placement within the tub such that the plurality of guide elements align and removably retain the at least one nest within the tub.

In some embodiments, the tub includes a top portion and a bottom portion, the bottom portion being dimensioned smaller than the top portion.

In some embodiments, the top portion is delineated by a bottom ledge surface and a top lid flange.

In some embodiments, a bottommost one of the at least one nest is at least partially supported by the bottom ledge surface of the tub.

In some embodiments, the plurality of guide elements extend along sidewall between the bottom ledge surface and the top lid flange.

In some embodiments, the plurality of guide elements include a plurality of rigid guide ribs.

In some embodiments, each of the plurality of rigid guide ribs includes a contact surface, and the contact surface of each of the plurality of rigid guide ribs includes an angle of inclination between the bottom ledge surface and the top lid flange.

In some embodiments, the angle of inclination of the contact surface is 1.0° or less.

In some embodiments, each of the plurality of rigid guide ribs is formed as a semi-cylindrical guide rib.

In some embodiments, the at least one nest further includes a plurality of opening portions formed thereon, and each of the plurality of opening portions are semi-circular in shape and are positioned and sized to substantially conform to an outer contour of the plurality of rigid guide ribs.

In some embodiments, the plurality of guide elements include a plurality of flexible ribs.

In some embodiments, each of the plurality of flexible ribs includes a proximal end portion coupled to the tub and a distal end portion decoupled from the tub.

In some embodiments, the plurality of guiding elements extend from a bottom surface of the tub, and the at least one nest includes a plurality of openings formed therein and sized and positioned so as to receive the plurality of guiding elements.

In some embodiments, the at least one nest further includes at least one finger opening formed therein.

In some embodiments, the at least one nest includes a plurality of nests, and the plurality of nests are configured to be stackable atop one another within the tub.

Further details and advantages of the present disclosure will be understood from the following detailed description read in conjunction with the accompanying drawings.

BRIEF DESCRIPTION OF THE DRAWINGS

FIG. 1 is a top isometric view of a nest and tub arrangement for the storage of plunger stoppers in accordance with an aspect of the present disclosure;

DESCRIPTION OF THE INVENTION

Figure 2A:
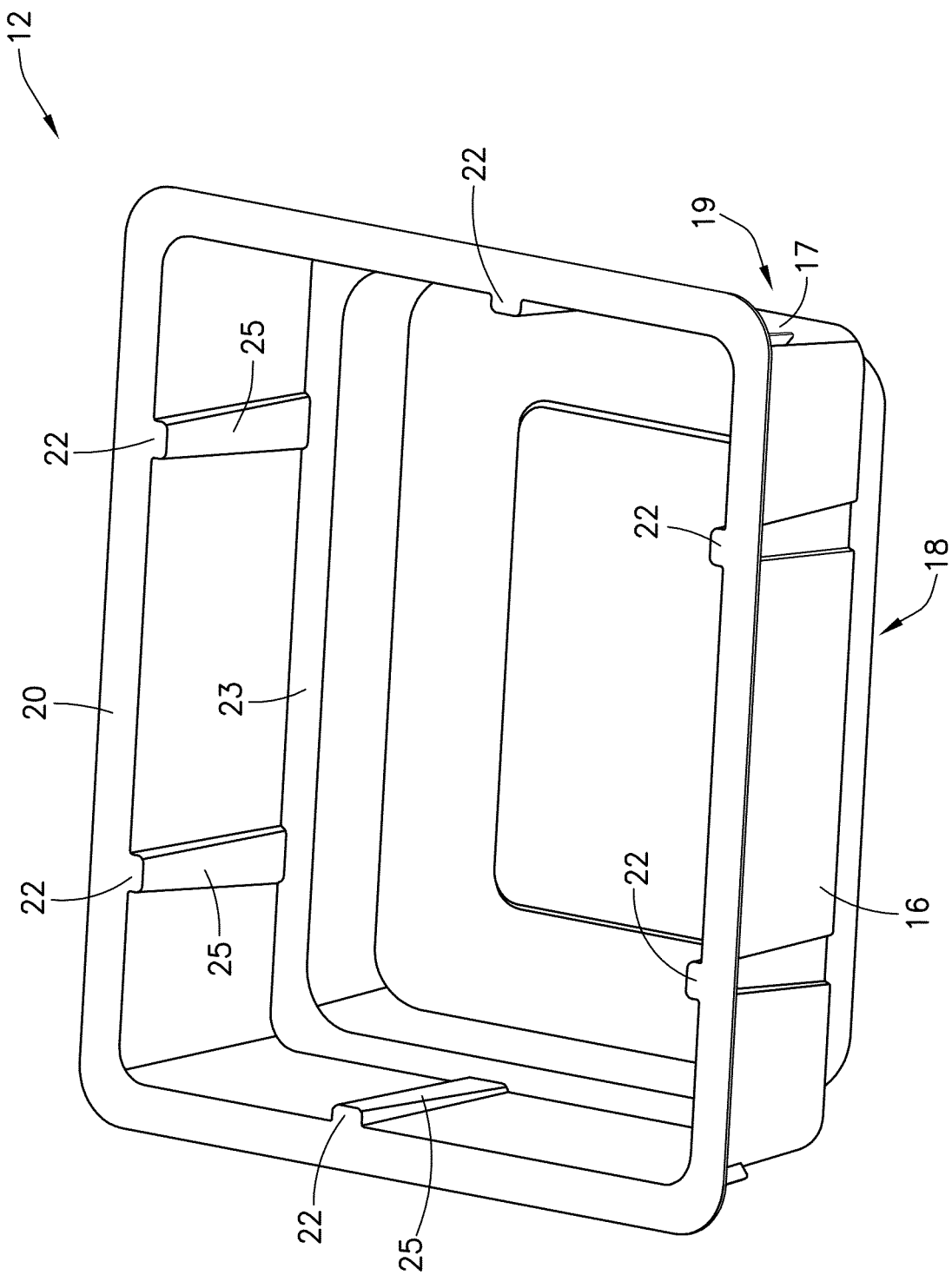
FIG. 2A is a top perspective view of a tub for use in the nest and tub arrangement of FIG. 1.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Referring to FIG. 1, a nest and tub arrangement 10 in accordance with an aspect of the present disclosure is shown. In the nest and tub arrangement 10, a plurality of nests 14 are capable of being removably retained within a tub 12, with each nest 14 configured to hold, e.g., a plurality of plunger stoppers (not shown). For example, the tub 12 may be configured to hold between two and ten nests 14, with the nests stacked vertically relative to one another. In one embodiment, the tub 12 is configured to hold seven nests 14.

As described above, various automated filling machines utilize other nest and tub arrangements in order to store and access medical device components such as, e.g., syringe barrels. Nest and tub arrangement 10, as shown in FIG. 1, is specifically configured to accommodate plunger stoppers in a way that provides for desired positioning and alignment of each nest 14 for accurate handling by the robotic components of the automated filling machines. However, it is to be understood that the present disclosure is not limited to use with plunger stoppers, as the nest and tub arrangements described herein may be utilized with other elements and/or devices.

Figure 2B:
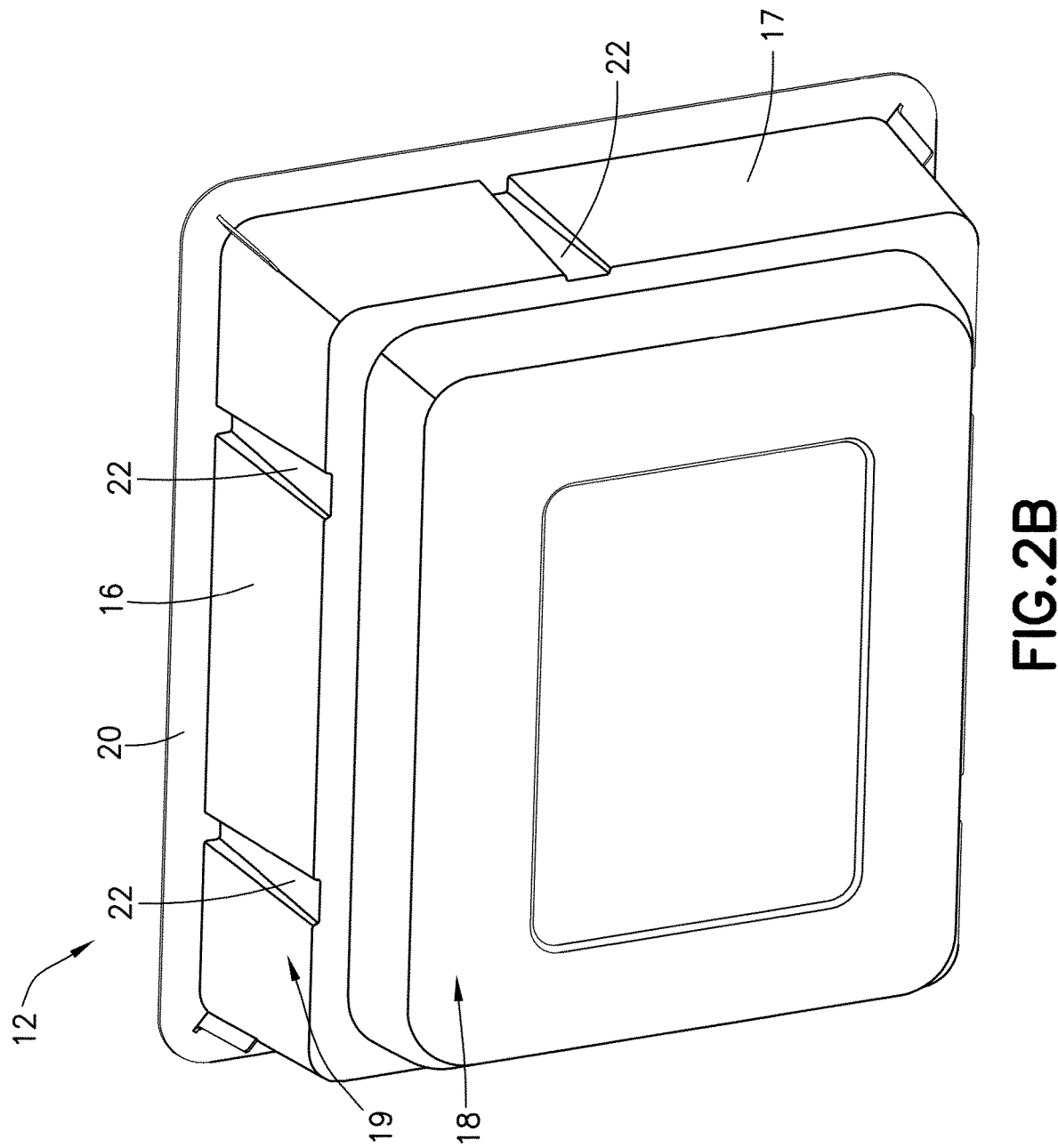
FIG. 2B is a bottom perspective view of the tub of FIG. 2A.

Referring still to FIG. 1, and also to FIGS. 2A and 2B, the tub 12 in accordance with an aspect of the present disclosure is shown. The tub 12 includes a pair of long side surfaces 16 and a pair of short side surfaces 17. However, in alternative embodiments, it is to be understood that the sides of tub 12 need not be different in length and/or parallel, and may instead be, e.g., equal, non-parallel, etc. The general dimensions of the tub 12 (i.e., length, width, and height) may be adapted based on the specific automated filling machine being utilized.

The tub 12 further includes a bottom portion 18 and a top portion 19. Bottom portion 18 is inset from top portion 19, with the bottom portion 18 being dimensioned smaller than the top portion 19, while top portion 19 is delineated by a top lid flange 20 and a bottom ledge surface 23. Bottom ledge surface 23 may be further considered to be a grip flange. Such a configuration enables a plurality of tubs 12 to be stacked together during storage, transport, etc., yet allows for sufficient spacing between the respective top lid flanges 20 of stacked tubs 12 so as to enable easy access to (and separation of) tubs 12. Additionally, as will be discussed in further detail below, the bottom ledge surface 23 is configured to provide a support surface for a bottommost nest 14 placed within the tub 12.

Tub 12 further includes a plurality of rigid guide ribs 22 extending into the interior of the tub 12 along respective side surfaces 16, 17 and substantially between the top lid flange 20 and the bottom ledge surface 23. In the embodiment shown in FIGS. 2A and 2B, the long side surfaces 16 each include two guide ribs 22, while short side surfaces 17 only include one guide rib 22, with each guide rib 22 on the short side surfaces 17 being laterally offset from one another. However, it is to be understood that more or fewer guide ribs 22 may be utilized on the respective side surfaces 16, 17. For example, in alternative embodiments of the present disclosure, the short side surfaces 17 may also include two guide ribs 22, the long side surfaces 16 may include three guide ribs 22, etc.

Each guide rib 22 includes an interior-facing contact surface 25 extending substantially from the top lid flange 20 to the bottom ledge surface 23. Each contact surface 25 is configured to provide a contact interface with a corresponding side surface of nests 14 in order to reliably align and removably retain the nests 14 within tub 12. In some embodiments, contact surface 25 is a substantially planar surface. Furthermore in some embodiments, the draft angle of each contact surface 25 of guide ribs 22 (i.e., the angle of inclination of the contact surface 25 between the bottom ledge surface 23 and the top lid flange 20) is relatively small, with the dimensions at the bottom ledge surface 23 being only marginally smaller than the dimensions at the top lid flange 20. For example, the draft angle of the contact surface 25 may be substantially less than 1° (e.g., 0.4°), even if the draft angle of the respective side surfaces 16, 17 of the tub 12 is larger than 1° (e.g., 1.2°). In this way, each of a plurality of nests 14 retained within the tub 12 may have a similar relative contact or spacing from the contact surfaces 25, thereby ensuring comparable alignment and retention of each nest 14, regardless of its vertical position within the top portion 19 of tub 12. In one embodiment, the positioning and draft angle of the respective contact surfaces 25 allows for a minimum amount of lateral "play" (i.e., back-and-forth lateral shifting) between the nests 14 and the tub 12 of between, e.g., 0.5 mm-0.9 mm.

Figure 3:
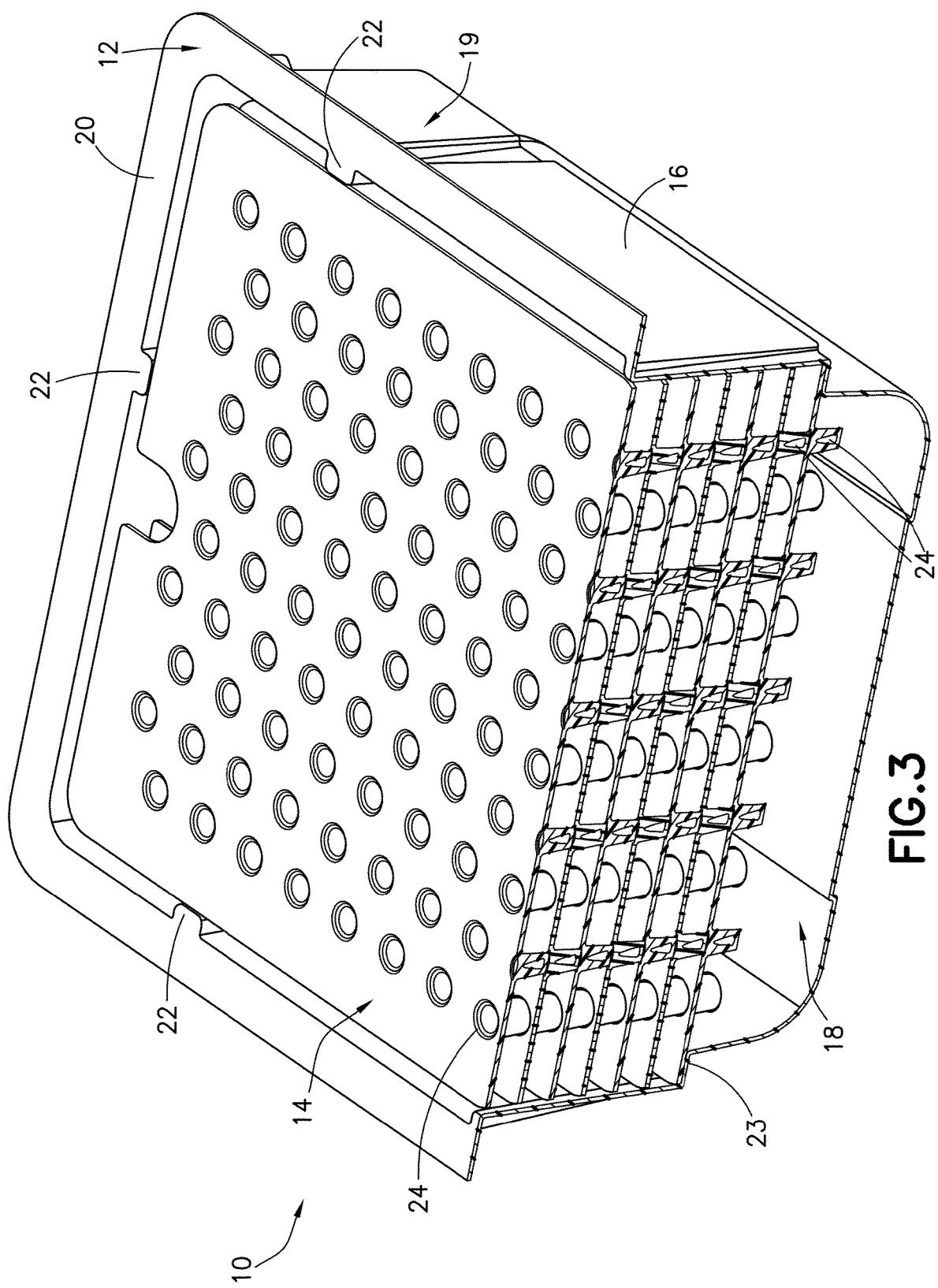
FIG. 3 is a cross-sectional isometric view of the nest and tub arrangement of FIG. 1.

Referring to FIG. 3, a cross-sectional view of the nest and tub arrangement 10 in accordance with an aspect of the present disclosure is shown. In the embodiment shown in FIG. 3, seven nests 14 are shown stacked within tub 12. The bottommost nest 14 is positioned adjacent the bottom ledge surface 23 of tub 12, and may be at least partially supported by the bottom ledge surface 23, while the uppermost nest 14 is positioned slightly below the top lid flange 20. Each stopper receptacle 24 may be vertically aligned with the stopper receptacle 24 above and below (if applicable). While the embodiment in FIG. 3 illustrates seven nests 14, it is to be understood that more or fewer nests may be held within the tub in other embodiments.

Referring still to FIGS. 1 and 3, each nest 14 is configured to hold a plurality of plunger stoppers, but it is to be understood that nest 14 may be configured to hold other components. Specifically, each nest 14 includes a plurality of stopper receptacles 24 formed therein. The stopper receptacles 24 may be formed as substantially frustoconical "chimneys", each capable of holding, e.g., a plunger stopper therein for access and removal by components of an autonomous filling machine. For example, during an assembly process, each nest 14 may be aligned atop a separate nest holding a plurality of syringes, and the autonomous filling machine may push each plunger stopper out of the stopper receptacles 24 and directly into a syringe positioned therebelow. The diameter and size of each stopper receptacle 24 may vary based on the type of stopper utilized during a particular filling operation. Thus, it is to be understood that the overall number and positioning of stopper receptacles 24 may also vary as compared to that which is shown in FIGS. 1 and 3.

Similar to tub 12 described above, each nest 14 includes a pair of long sides 28 and a pair of short sides 29. However, in alternative embodiments, it is to be understood that the sides of nest 14 need not be different in length and/or parallel, and may instead be, e.g., equal, non-parallel, etc. Also, like tub 12, the general dimensions of each nest 14 (i.e., length, width, and height) may be adapted based on the specific automated filling machine being utilized.

Furthermore, as shown in FIG. 1, the short sides 29 of each nest 14 may include a finger opening 26 formed thereon, wherein each finger opening 26 is designed to enable simplified manual loading (and/or removal) of the nest 14 into (or from) the tub 12. In some embodiments, a flange (not shown) may at least partially surround each finger opening 26 and extend from a bottom surface of nest 14, thereby providing the user with a larger surface area upon which to grip the nest 14. While two finger openings 26 are shown on opposing short sides 29 in FIG. 1, it is to be understood that nest 14 may include more or fewer finger openings, either on short sides 29 or long sides 28. Additionally, in some embodiments, the finger openings 26 may be omitted altogether.

Tub 12 may be formed of any suitable material, and via any suitable method. For example, tub 12 may be formed of, e.g., a plastic, polymer (e.g., polystyrene), metal, etc., and may be formed by, e.g., molding (e.g., injection molding), thermoforming, stamping, extrusion, welding, etc. Furthermore, tub 12 may be formed as a single piece, or as multiple pieces coupled together. If formed of multiple pieces, the materials forming each piece may be the same or different. Additionally, the guide ribs 22 may be formed as part of the tub 12, or may be formed separately from the tub 12. If formed separately, the guide ribs 22 may be coupled to the tub 12 via any appropriate method such as, e.g., an adhesive, one or more fasteners, welding, etc.

Similarly, each nest 14 may be formed of any suitable material, and via any suitable method. For example, nest 14 may be formed of, e.g., a plastic, polymer (e.g., polypropylene, polystyrene, etc.), metal, etc., and may be formed by, e.g., molding (e.g., injection molding), thermoforming, stamping, extrusion, welding, etc. Furthermore, nest 14 may be formed as a single piece, or as multiple pieces coupled together. If formed of multiple pieces, the materials forming each piece may be the same or different.

With the nest and tub arrangement 10 shown and described with respect to FIGS. 1-3, a plurality of plunger stoppers may be held in a plurality of nests 14, with each nest 14 being removably retained within a tub 12. In this way, the nest and tub arrangement 10 may be utilized by various automated filling machines that necessitate precise alignment, minimal "play" of both components and their storage means, and ready access to syringe components, including plunger stoppers.

Figure 4A:
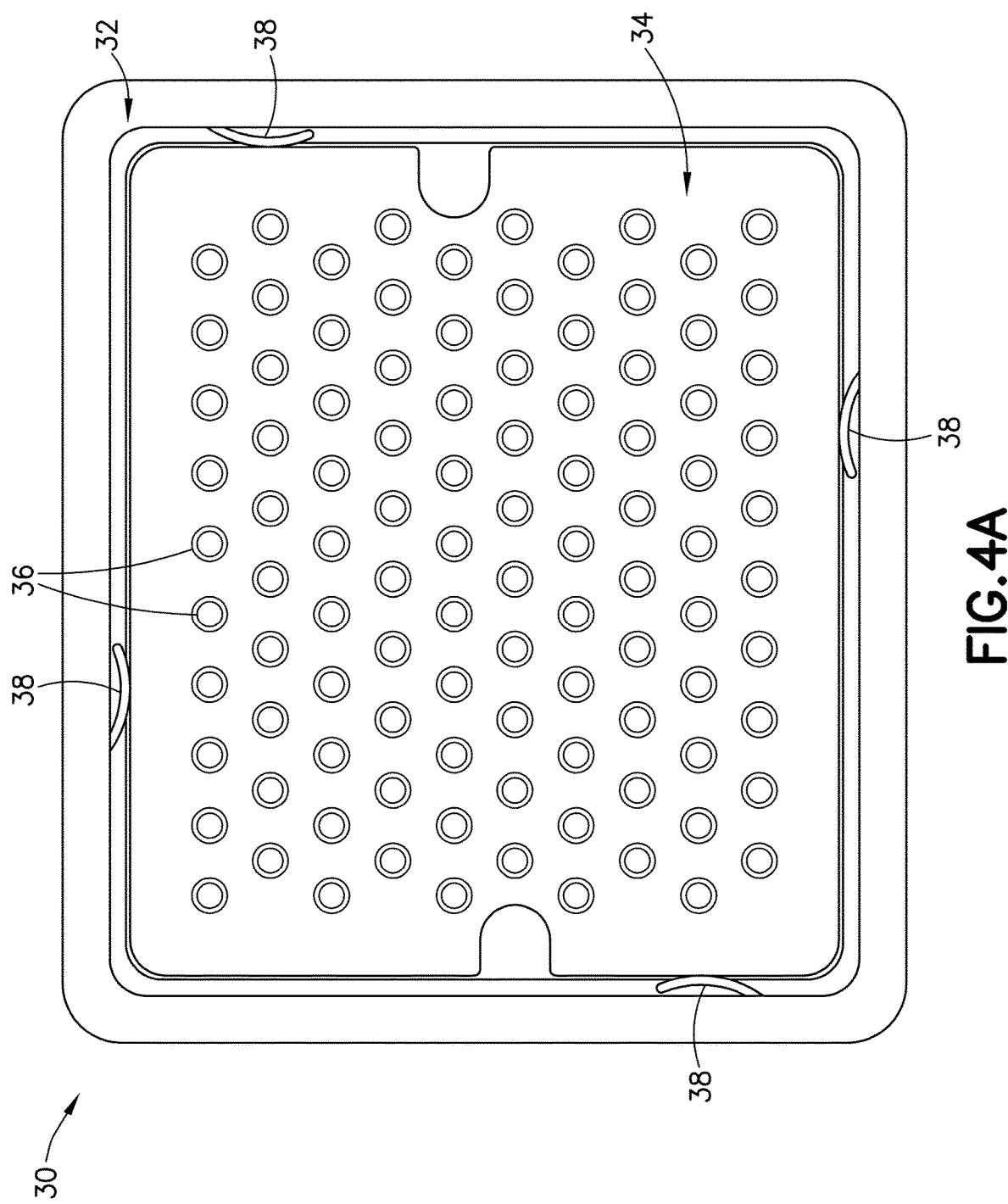
FIG. 4A is a top plan view of a nest and tub arrangement for the storage of plunger stoppers in accordance with another aspect of the present disclosure.
Figure 4B:
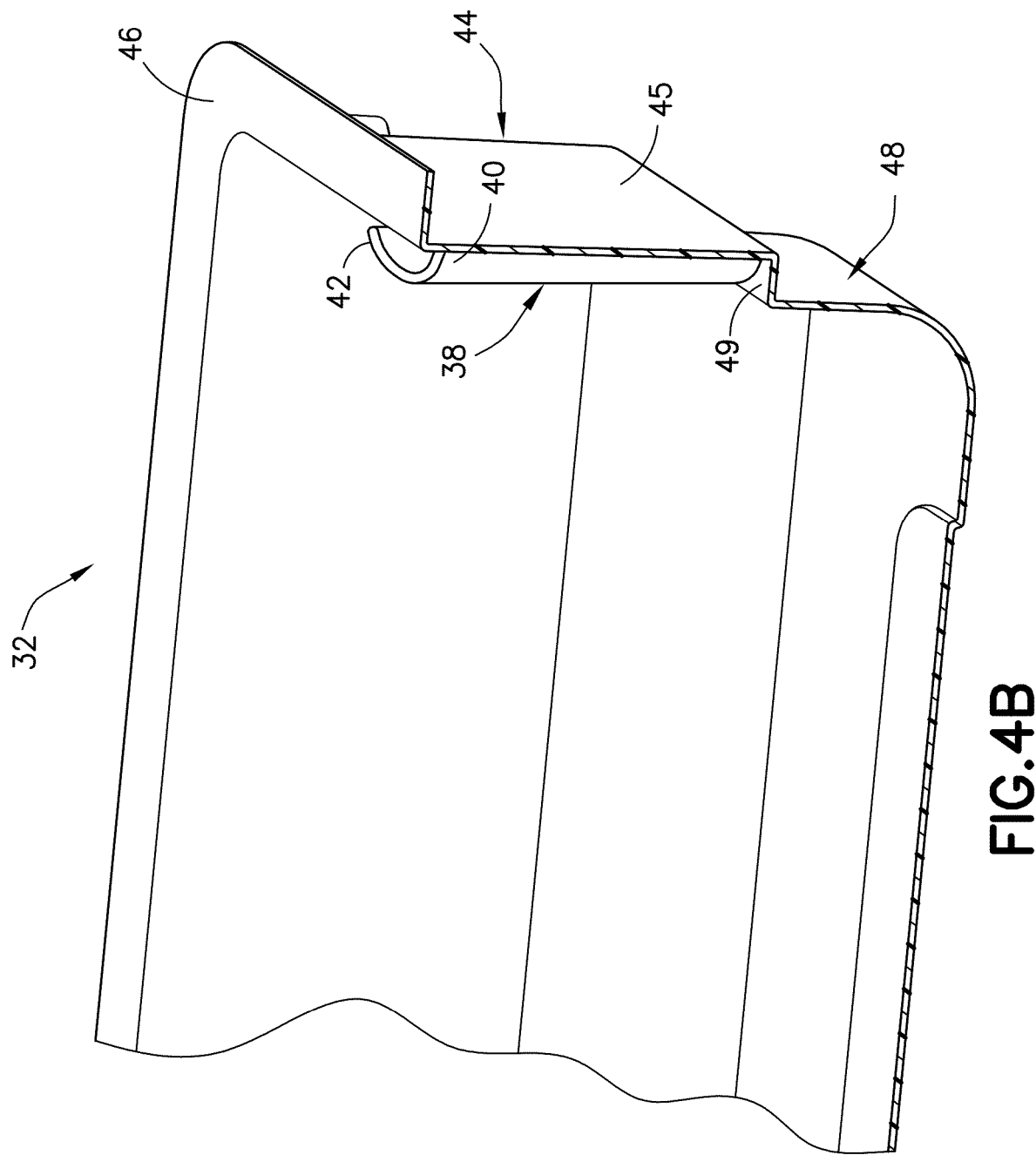
FIG. 4B is a partial isometric and cross-sectional view of a tub for use in the nest and tub arrangement of FIG. 4A.
Figure 4C:
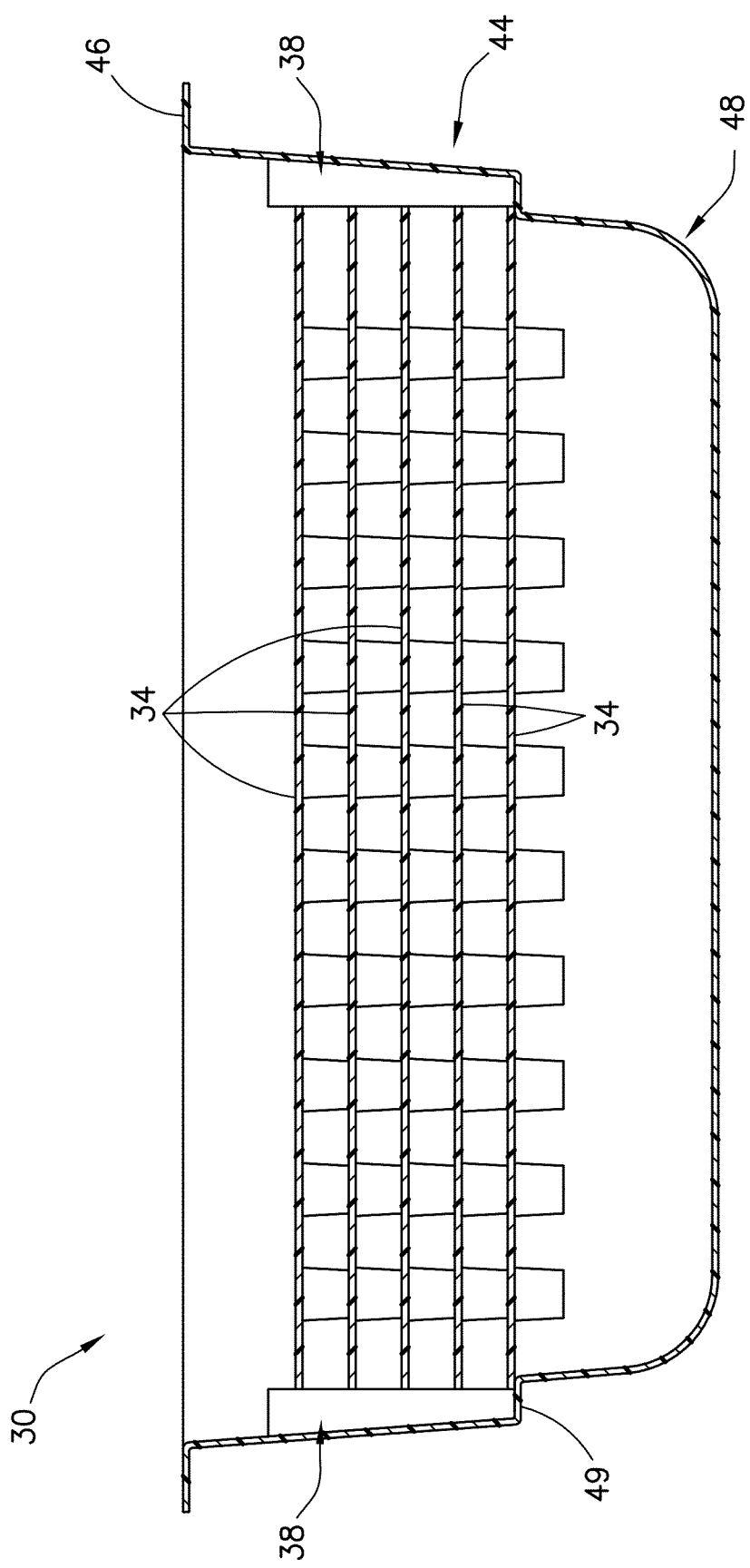
FIG. 4C is a cross-sectional view of the nest and tub arrangement of FIG. 4A.

Next, referring to FIGS. 4A-4C, a nest and tub arrangement 30 in accordance with another aspect of the present disclosure is illustrated. Similar to nest and tub arrangement 10 described above with respect to FIGS. 1-3, in the nest and tub arrangement 30, a plurality of nests 34 are capable of being removably retained within a tub 32, with each nest 34 configured to hold, e.g., a plurality of plunger stoppers (not shown) within a plurality of stopper receptacles 36. For example, the tub 32 may be configured to hold between two and ten nests 34, with the nests stacked vertically relative to one another. In one embodiment, the tub 32 is configured to hold seven nests 34. The overall structure and purpose of nest and tub arrangement 30 is substantially similar to nest and tub arrangement 10. As such, not all details of the construction of tub 32 and/or nest 34 will be described herein.

Referring to FIG. 4B, the tub 32 further includes a bottom portion 48 and a top portion 44. Bottom portion 48 is inset from top portion 44, with the bottom portion 48 being dimensioned smaller than the top portion 44, while top portion 44 is delineated by a top lid flange 46 and a bottom ledge surface 49. Furthermore, the tub 32 includes a plurality of flexible ribs 38 extending into the interior of the tub 32 along respective side surfaces of the tub 32 and substantially between the top lid flange 46 and the bottom ledge surface 49. In the embodiment shown in FIG. 4A, each side surfaces of the tub 32 includes a single flexible rib 38, with opposite flexible ribs 38 being laterally offset from one another. However, it is to be understood that more or fewer flexible ribs 38 may be utilized on the respective side surfaces, and the flexible ribs 38 need not be laterally offset from one another.

As is shown in FIG. 4B, each flexible rib 38 includes a proximal end portion 40 and a distal end portion 42. The proximal end portion 40 is coupled to a sidewall 45 of the top portion 44, while the distal end portion 42 is free and decoupled from the sidewall 45. In this way, the flexible rib 38 forms, e.g., a substantially C-shaped rib that is laterally deflectable about the proximal end portion 40. In view of each flexible rib 38 being deflectable in this manner, the respective side surfaces of each nest 34 may be configured to contact a respective flexible rib 38 when inserted into tub 32, with the flexible ribs 38 deflecting and providing a slight compressive force on the nests 34. Accordingly, the flexible ribs 38 are able to compensate for the standard draft angle and undercut of the tub 32 to maintain each of the nests 34 in a substantially centered position within the tub 32, with little to no lateral "play" of the nests 34.

Referring to FIG. 4C, a cross-sectional view of the nest and tub arrangement 30 in accordance with an aspect of the present disclosure is shown. A plurality of nests 34 are shown vertically stacked within tub 32, with the bottommost nest 34 positioned adjacent the bottom ledge surface 49 of tub 32 such that it is at least partially supported by the bottom ledge surface 49. While the embodiment in FIG. 4C illustrates four nests 34, it is to be understood that more or fewer nests may be held within the tub in other embodiments.

Additionally, while not shown in FIGS. 4A-4C, it is to be understood that each nest 34 may include one or more finger openings formed thereon to enable simplified manual loading (and/or removal) of the nest 34 into (or from) the tub 32, similar to finger openings 26 described above with respect to FIGS. 1-3. Conversely, in some embodiments, the finger opening(s) may be omitted altogether.

Tub 32 may be formed of any suitable material, and via any suitable method. For example, tub 32 may be formed of, e.g., a plastic, polymer (e.g., polystyrene), metal, etc., and may be formed by, e.g., molding (e.g., injection molding), thermoforming, stamping, extrusion, welding, etc. Furthermore, tub 32 may be formed as a single piece, or as multiple pieces coupled together. If formed of multiple pieces, the materials forming each piece may be the same or different. Additionally, the flexible ribs 38 may be formed as part of the tub 32, or may be formed separately from the tub 32. If formed separately, the flexible ribs 38 may be coupled to the tub 32 via any appropriate method such as, e.g., an adhesive, one or more fasteners, welding, etc.

Similarly, each nest 34 may be formed of any suitable material, and via any suitable method. For example, each nest 34 may be formed of, e.g., a plastic, polymer (e.g., polypropylene, polystyrene, etc.), metal, etc., and may be formed by, e.g., molding (e.g., injection molding), thermoforming, stamping, extrusion, welding, etc. Furthermore, each nest 34 may be formed as a single piece, or as multiple pieces coupled together. If formed of multiple pieces, the materials forming each piece may be the same or different.

Figure 5A:
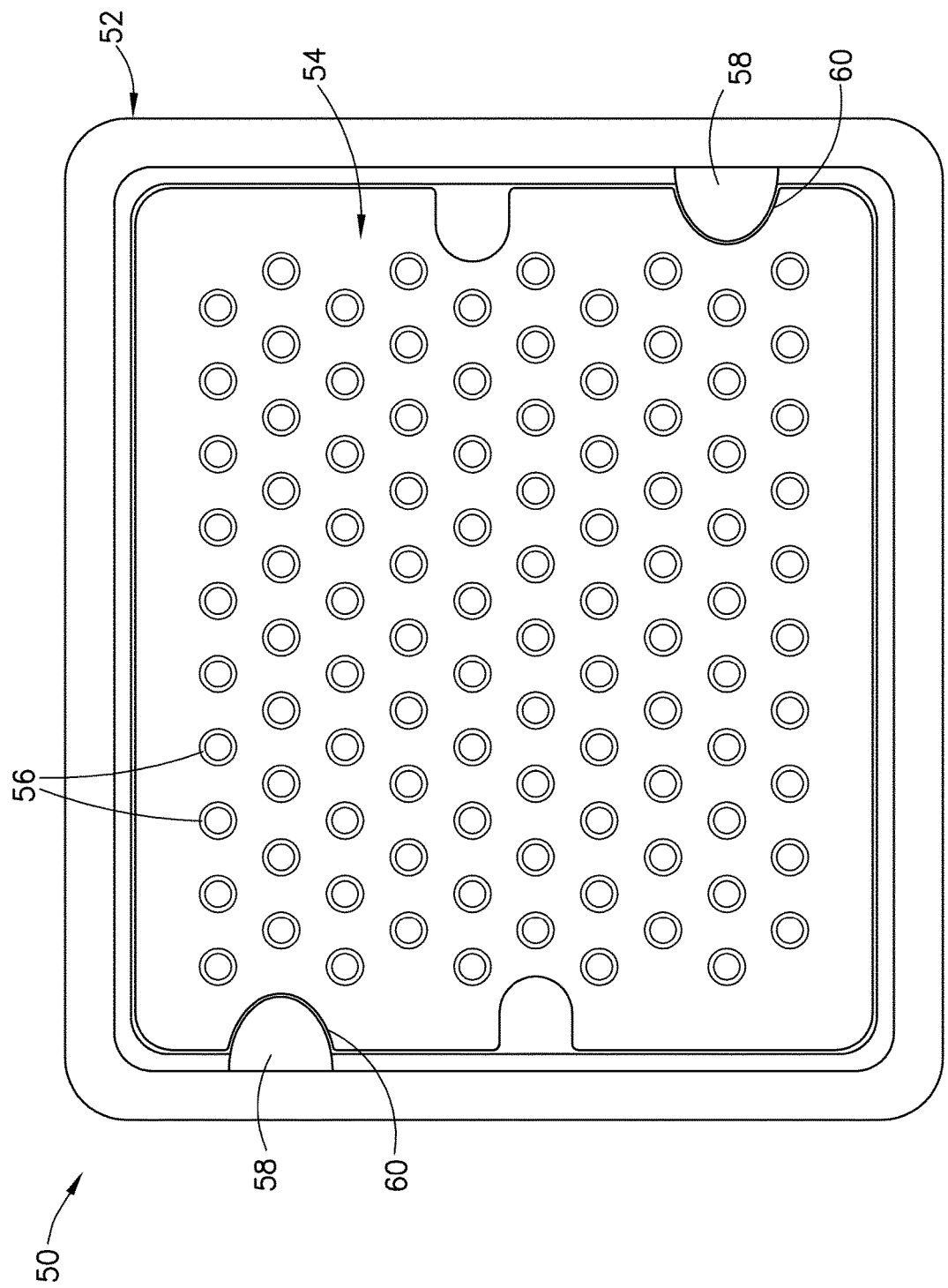
FIG. 5A is a top plan view of a nest and tub arrangement for the storage of plunger stoppers in accordance with another aspect of the present disclosure.
Figure 5B:
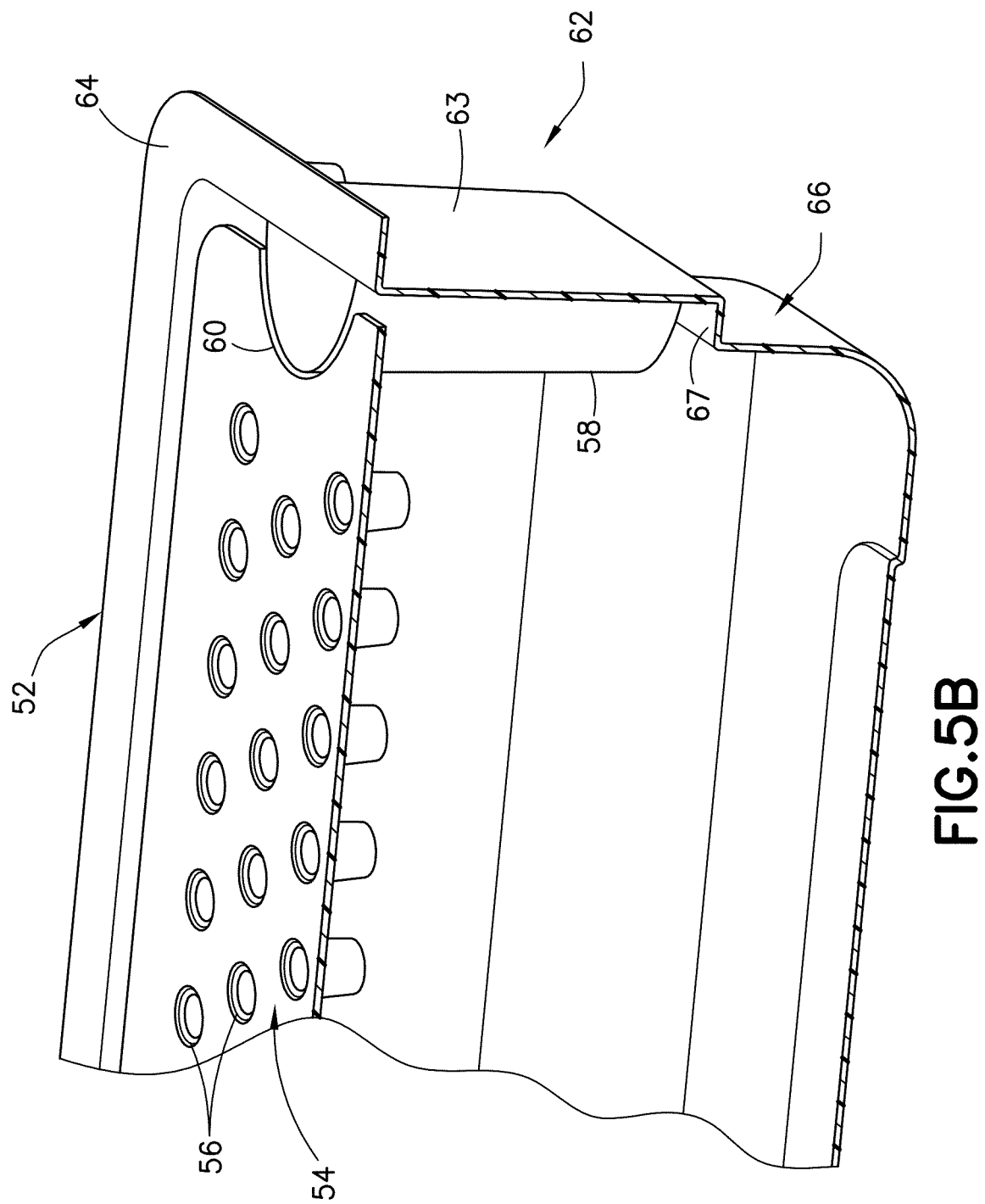
FIG. 5B is a partial isometric and cross-sectional view of the nest and tub arrangement of FIG. 5A.

Next, referring to FIGS. 5A and 5B, a nest and tub arrangement 50 in accordance with another aspect of the present disclosure is illustrated. Similar to the nest and tub arrangements described above with respect to FIGS. 1-3 and FIGS. 4A-4C, respectively, in the nest and tub arrangement 50, a plurality of nests 54 are capable of being removably retained within a tub 52, with each nest 54 configured to hold, e.g., a plurality of plunger stoppers (not shown) within a plurality of stopper receptacles 56. For example, the tub 52 may be configured to hold between two and ten nests 54, with the nests stacked vertically relative to one another. In one embodiment, the tub 52 is configured to hold seven nests 54. The overall structure and purpose of nest and tub arrangement 50 is substantially similar to nest and tub arrangements 10, 30. As such, not all details of the construction of tub 52 and/or nest 54 will be described herein.

Referring to FIG. 5B, the tub 52 includes a bottom portion 66 and a top portion 62. Bottom portion 66 is inset from top portion 62, with the bottom portion 66 being dimensioned smaller than the top portion 62, while top portion 62 is delineated by a top lid flange 64 and a bottom ledge surface 67.

Furthermore, the tub 52 includes a plurality of prominent rigid ribs 58 extending into the interior of the tub 52 along at least two side surfaces 63 of the tub 52 and substantially between the top lid flange 64 and the bottom ledge surface 67. In the embodiment shown in FIG. 5A, two opposite side surfaces of the tub 52 include a rigid rib 58, with the rigid ribs 58 being laterally offset from one another. However, it is to be understood that more or fewer rigid ribs 58 may be utilized on the respective side surfaces. Furthermore, the rigid ribs 58 need not be laterally offset from one another.

As is shown in FIG. 5B, each rigid rib 58 is substantially semi-cylindrical in shape and extends into the interior of the tub 52 across substantially the entire width of the bottom ledge surface 67. However, it is to be understood that the rigid rib 58 is not limited to such a semi-cylindrical shape, and may be any appropriate size(s) and/or shape(s).

Correspondingly, each nest 54 is configured to include an opening portion 60 formed in one or more side surfaces thereof, wherein the opening portion(s) 60 are shaped and configured so as to substantially match the outer contour of the rigid rib 58. In FIGS. 5A and 5B, opening portions 60 are shown as being semi-circular in shape so as to substantially match the outer contour of the rigid rib 58. However, it is to be understood that opening portions 60 are not limited to such a semi-circular shape, and may be any appropriate shape and size which corresponds to the outer contour of the rigid ribs 58.

In this way, one or more nests 54 can be stacked and retained within the tub 52, with each nest 54 having comparable alignment and retention within the tub 52, regardless of its vertical position within the top portion 62 of tub 52. In one embodiment, the size and positing of each opening portion 60 in the nests 54 allows for a minimal amount of lateral "play" (i.e., back-and-forth lateral shifting) between the nests 54 and the tub 52 (e.g., between 0.5 mm-0.9 mm).

While not shown in FIGS. 5A and 5B, it is to be understood that a plurality of nests 54 may be vertically stacked within tub 52, with the bottommost nest 54 being positioned adjacent the bottom ledge surface 67 such that it is at least partially supported by the bottom ledge surface 67. Additionally, it is to be understood that each nest 54 may include one or more finger openings formed thereon to enable simplified manual loading (and/or removal) of the nest 54 into (or from) the tub 52, similar to finger openings 26 described above with respect to FIGS. 1-3. Conversely, in some embodiments, the finger opening(s) may be omitted altogether.

Tub 52 may be formed of any suitable material, and via any suitable method. For example, tub 52 may be formed of, e.g., a plastic, polymer (e.g., polystyrene), metal, etc., and may be formed by, e.g., molding (e.g., injection molding), thermoforming, stamping, extrusion, welding, etc. Furthermore, tub 52 may be formed as a single piece, or as multiple pieces coupled together. If formed of multiple pieces, the materials forming each piece may be the same or different. Additionally, the rigid ribs 58 may be formed as part of the tub 52, or may be formed separately from the tub 52. If formed separately, the rigid ribs 58 may be coupled to the tub 52 via any appropriate method such as, e.g., an adhesive, one or more fasteners, welding, etc.

Similarly, each nest 54 may be formed of any suitable material, and via any suitable method. For example, each nest 54 may be formed of, e.g., a plastic, polymer (e.g., polypropylene, polystyrene, etc.), metal, etc., and may be formed by, e.g., molding (e.g., injection molding), thermoforming, stamping, extrusion, welding, etc. Furthermore, each nest 54 may be formed as a single piece, or as multiple pieces coupled together. If formed of multiple pieces, the materials forming each piece may be the same or different.

Figure 6A:
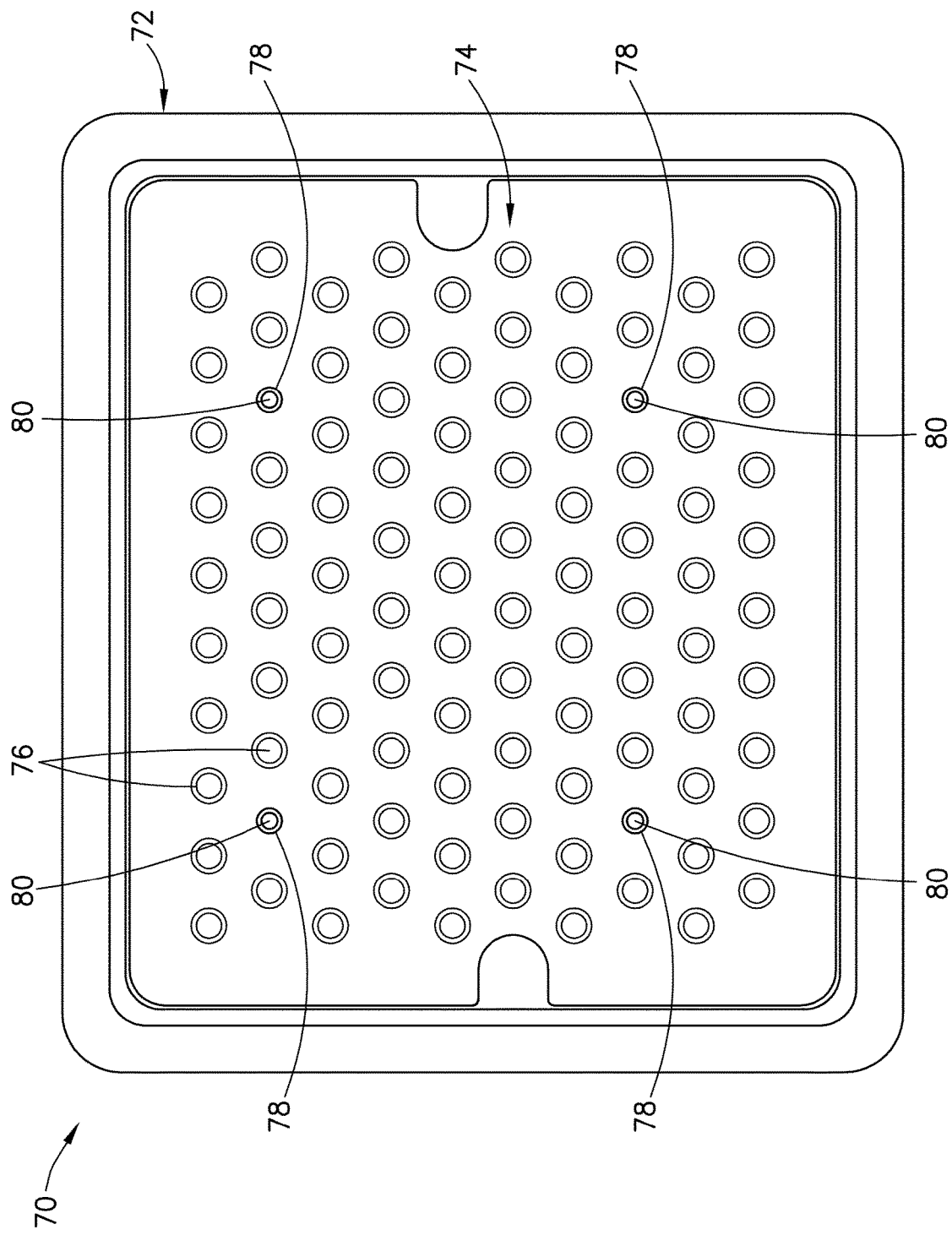
FIG. 6A is a top plan view of a nest and tub arrangement for the storage of plunger stoppers in accordance with another aspect of the present disclosure.
Figure 6B:
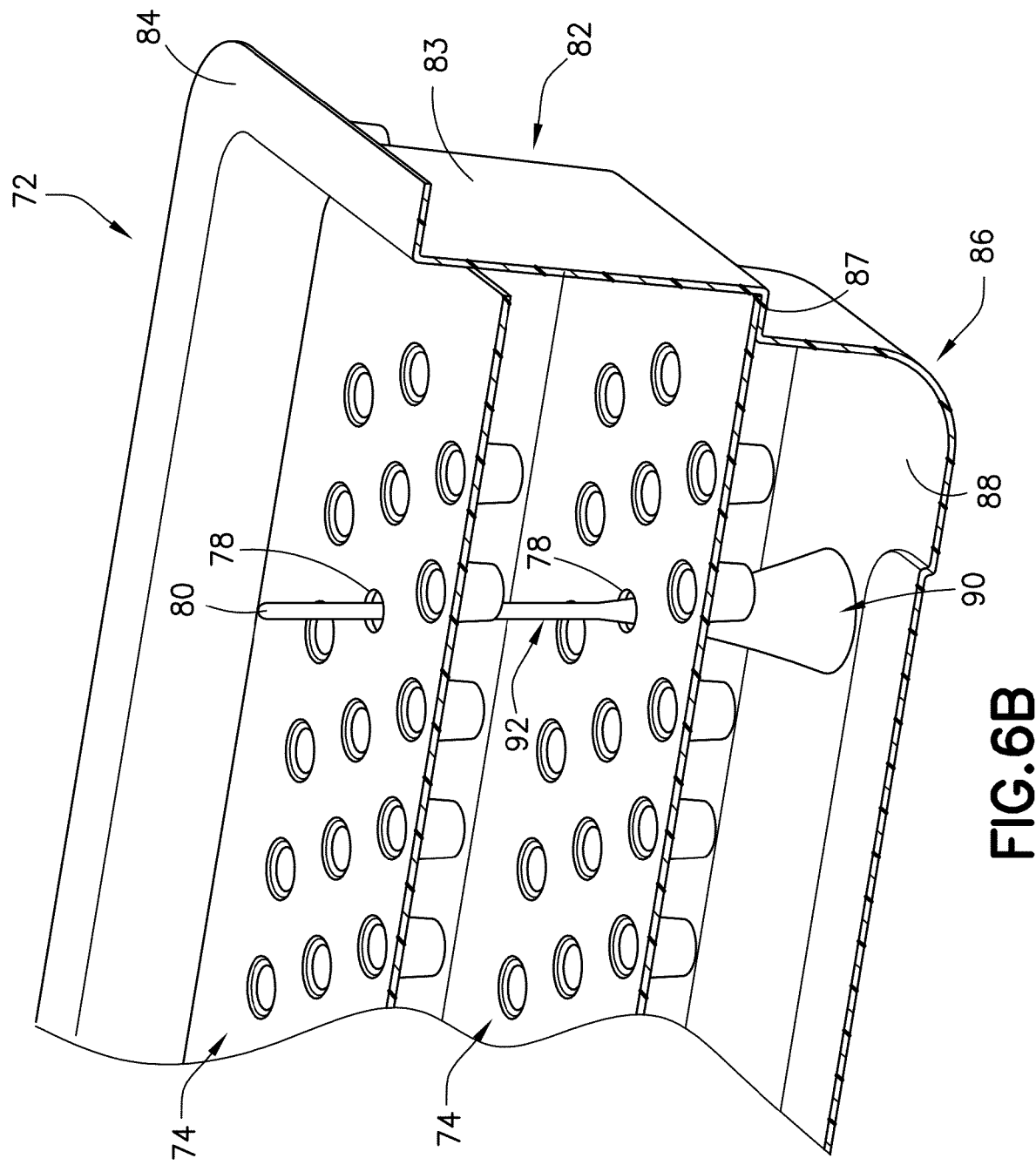
FIG. 6B is a partial isometric and cross-sectional view of the nest and tub arrangement of FIG. 6A.
Figure 6C:
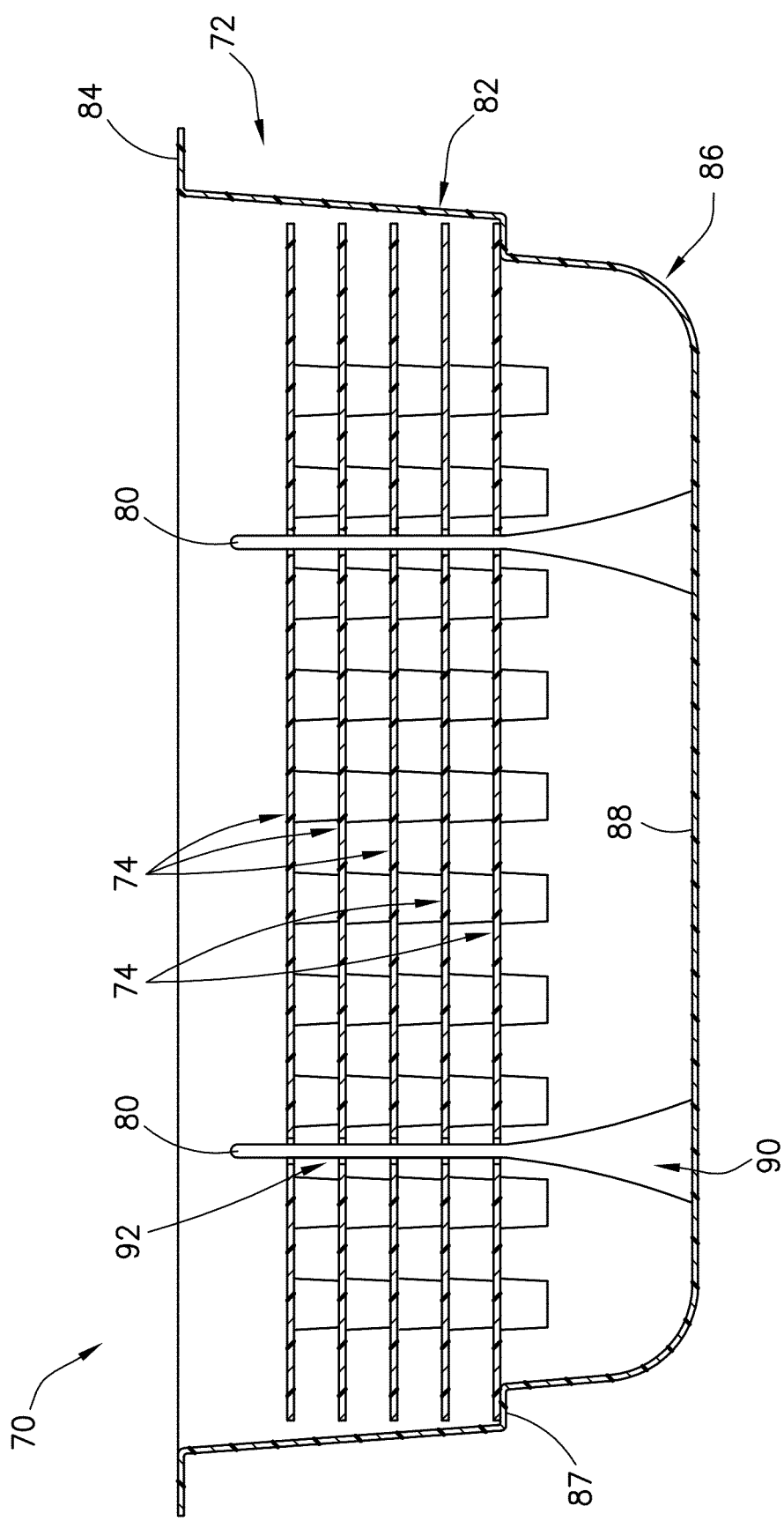
FIG. 6C is a cross-sectional view of the nest and tub arrangement of FIG. 6A.

Next, referring to FIGS. 6A-6C, a nest and tub arrangement 70 in accordance with another aspect of the present disclosure is illustrated. As with the nest and tub arrangements described above with respect to FIGS. 1-3, FIGS. 4A-4C, and FIGS. 5A and 5B, respectively, in the nest and tub arrangement 70, a plurality of nests 74 are capable of being removably retained within a tub 72, with each nest 74 configured to hold, e.g., a plurality of plunger stoppers (not shown) within a plurality of stopper receptacles 76. For example, the tub 72 may be configured to hold between two and ten nests 74, with the nests stacked vertically relative to one another. In one embodiment, the tub 72 is configured to hold seven nests 74. The overall structure and purpose of nest and tub arrangement 70 is substantially similar to the nest and tub arrangements described above. As such, not all details of the construction of tub 72 and/or nest 74 will be described herein.

Referring to FIG. 6B, the tub 72 further includes a bottom portion 86 and a top portion 82. Bottom portion 86 is inset from top portion 82, with the bottom portion 86 being dimensioned smaller than the top portion 82, while top portion 82 is delineated by a top lid flange 84 and a bottom ledge surface 87, with a sidewall 83 running substantially therebetween.

Furthermore, as is shown in FIGS. 6B and 6C, the tub 72 includes a plurality of rigid shafts 80 extending upward into the interior of the tub 72 from a bottom surface 88 of the tub 72. In the embodiment shown in FIG. 6A, four rigid shafts 80 are shown extending from the bottom surface 88, with the rigid shafts 80 being substantially equally spaced relative to one another within the tub 72. However, it is to be understood that more or fewer rigid shafts 80 may be utilized, and the rigid shafts 80 need not be equally spaced relative to one another.

As is also shown in FIGS. 6B and 6C, each rigid shaft 80 is at least partially cylindrical in shape. Specifically, each rigid shaft 80 may include a substantially flared bottom portion 90 and a narrower top portion 92. With such a configuration, the strength of the rigid shaft 80 with respect to the bottom surface 88 of the nest 72 may be increased, while still allowing the top portion 92 to be substantially uniform in shape. However, it is to be understood that the rigid shaft 80 is not limited to such a shape and configuration, and may be any appropriate shape (or shapes).

Correspondingly, each nest 74 is configured to include a plurality of openings 78 formed therethrough. Each of the openings 78 are configured to be placed between the stopper receptacles 76, with the number and position of openings 78 corresponding to the relative number and position of the rigid shafts 80 within the tub 72. The openings 78 are shaped and configured so as to be slightly larger than the outer contour of the rigid shafts 80. In this way, one or more nests 74 can be stacked and retained within the tub 72 via placement of the respective openings 78 over the rigid shafts 80. Accordingly, each nest 74 will have comparable alignment and retention within the tub 72, regardless of its vertical position within the tub 72.

As is shown in FIG. 6C, in one embodiment, the bottommost nest 74 is positioned adjacent the bottom ledge surface 87 of the tub 72 such that it is at least partially supported by the bottom ledge surface 87. Additionally, as is also shown in FIGS. 6B and 6C, because the sides of the respective nests 74 are substantially spaced-apart from the sidewall 83 of the top portion 82, there is no need for finger openings to be provided in or on the nests 74 to enable simplified manual loading (and/or removal) of the nests 74 to (or from) the tub 72, as there is sufficient space provided. However, in alternative embodiments, it is to be understood that each nest 74 may include one or more finger openings formed thereon to enable simplified manual loading (and/or removal) of the nest 74 into (or from) the tub 72, similar to finger openings 26 described above with respect to FIGS. 1-3.

Tub 72 may be formed of any suitable material, and via any suitable method. For example, tub 72 may be formed of, e.g., a plastic, polymer (e.g., polystyrene), metal, etc., and may be formed by, e.g., molding (e.g., injection molding), thermoforming, stamping, extrusion, welding, etc. Furthermore, tub 72 may be formed as a single piece, or as multiple pieces coupled together. If formed of multiple pieces, the materials forming each piece may be the same or different. Additionally, the rigid shafts 80 may be formed as part of the tub 72, or may be formed separately from the tub 72. If formed separately, the rigid shafts 80 may be coupled to the tub 72 via any appropriate method such as, e.g., an adhesive, one or more fasteners, welding, etc.

Similarly, each nest 74 may be formed of any suitable material, and via any suitable method. For example, each nest 74 may be formed of, e.g., a plastic, polymer (e.g., polypropylene, polystyrene, etc.), metal, etc., and may be formed by, e.g., molding (e.g., injection molding), thermoforming, stamping, extrusion, welding, etc. Furthermore, each nest 74 may be formed as a single piece, or as multiple pieces coupled together. If formed of multiple pieces, the materials forming each piece may be the same or different.

While several embodiments of a nest and tub arrangement are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A nest and tub arrangement for the storage of medical device components, comprising:
   a tub comprising a plurality of guide elements extending from at least one surface of the tub and into the interior of the tub, wherein the plurality of guide elements comprises a plurality of flexible ribs and a plurality of rigid guide ribs; and
   at least one nest comprising a plurality of receptacles for the storage of a plurality of medical device components therein, wherein the at least one nest is sized and configured for placement within the tub such that the plurality of guide elements align and removably retain the at least one nest within the tub,
   wherein the at least one nest further comprises a plurality of opening portions formed thereon, and wherein each of the plurality of opening portions are semi-circular in shape and are positioned and sized to substantially conform to an outer contour of the plurality of rigid guide ribs, and wherein side surfaces of the at least one nest contact the plurality of flexible ribs when inserted into the tub, with the plurality of flexible ribs deflecting and providing a compressive force on the at least one nest.

2. The nest and tub arrangement according to claim 1, wherein the tub comprises a top portion and a bottom portion, the bottom portion being dimensioned smaller than the top portion.

3. The nest and tub arrangement according to claim 2, wherein a bottommost one of the at least one nest is at least partially supported by the bottom ledge surface of the tub.

4. The nest and tub arrangement according to claim 2, wherein the top portion is delineated by a bottom ledge surface and a top lid flange.

5. The nest and tub arrangement according to claim 4, wherein the plurality of guide elements extend along a sidewall of the tub between the bottom ledge surface and the top lid flange.

6. The nest and tub arrangement according to claim 1, wherein each of the plurality of rigid guide ribs comprises a contact surface, and wherein the contact surface of each of the plurality of rigid guide ribs comprises an angle of inclination between the bottom ledge surface and the top lid flange.

7. The nest and tub arrangement according to claim 6, wherein the angle of inclination of the contact surface is 1.0° or less.

8. The nest and tub arrangement according to claim 1, wherein each of the plurality of rigid guide ribs is formed as a semi-cylindrical guide rib.

9. The nest and tub arrangement according to claim 1, wherein the plurality of guiding elements comprise rigid shafts that extend from a bottom surface of the tub, and further wherein the at least one nest comprises a plurality of shaft openings formed therein and sized and positioned so as to receive the rigid shafts.

10. The nest and tub arrangement according to claim 1, wherein the at least one nest further comprises at least one finger opening formed therein.

11. The nest and tub arrangement according to claim 1, wherein the at least one nest comprises a plurality of nests and further wherein the plurality of nests are configured to be stackable atop one another within the tub.

12. A nest and tub arrangement for the storage of medical device components, comprising:
   a tub comprising a plurality of guide elements extending from at least one surface of the tub and into the interior of the tub, wherein the plurality of guide elements comprises a plurality of flexible ribs and a plurality of rigid guide ribs; and
   at least one nest comprising a plurality of receptacles for the storage of a plurality of medical device components therein, wherein the at least one nest is sized and configured for placement within the tub such that the plurality of guide elements align and removably retain the at least one nest within the tub,
   wherein the at least one nest further comprises a plurality of opening portions formed thereon, and wherein each of the plurality of opening portions are semi-circular in shape and are positioned and sized to substantially conform to an outer contour of the plurality of rigid guide ribs,
   wherein each of the plurality of flexible ribs comprises a proximal end portion coupled to the tub and a distal end portion decoupled from the tub.

* * * * *